US005593881A

United States Patent [19]
Thompson et al.

[11] Patent Number: 5,593,881
[45] Date of Patent: Jan. 14, 1997

[54] BACILLUS THURINGIENSIS DELTA-ENDOTOXIN

[75] Inventors: Mark Thompson, San Diego; George E. Schwab, Encinitas; H. Ernest Schnepf; Brian Stockhoff, both of San Diego, all of Calif.

[73] Assignee: Mycogen Corporation, San Diego, Calif.

[21] Appl. No.: 239,474

[22] Filed: May 6, 1994

[51] Int. Cl.$^6$ .............................. C12N 5/10; C12N 15/63; C07H 21/04
[52] U.S. Cl. .................... 435/240.1; 435/252.3; 435/320.1; 536/23.71
[58] Field of Search ............................ 435/320.1, 240.2, 435/91.1, 91.4, 91.41, 91.42, 240.1, 252.3; 536/23.1, 23.7, 23.71, 24.1, 24.2

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,797,276 | 1/1989 | Hermstadt et al. | 424/84 |
| 4,849,217 | 7/1989 | Soares et al. | 424/93.461 |
| 4,853,331 | 8/1989 | Hermstadt et al. | 435/252.3 |
| 4,918,006 | 4/1990 | Ellar et al. | 435/69.1 |
| 4,948,734 | 8/1990 | Edwards et al. | 514/2 |
| 5,055,294 | 10/1991 | Gilroy | 424/93.2 |
| 5,128,130 | 7/1992 | Gilroy et al. | 424/93.2 |
| 5,151,363 | 9/1992 | Payne | 435/252.5 |
| 5,208,077 | 5/1993 | Proctor et al. | 427/461 |

FOREIGN PATENT DOCUMENTS 9506730  3/1995  WIPO .

OTHER PUBLICATIONS

Nakamura,. et al. (1990) "Construction of Chimeric Insecticidal Proteins between the 130–kDa and 135–kDa Proteins of *Bacillus thuringiensis* subsp. *aizawai* for Analysis of Structure–Function Relationship" Agric. Biol. Chem. 54(3):715–724.

Raymond, K. C. et al. (1990) "Larvicidal activity of chimeric *Bacillus thuringiensis* protoxins" Molecular Microbiology 4(11);1967–1973.

Stiekema, W. et al. (1990) "Recombinant *Baccillus thuringiensis* Crystal Protein Genes and their Entomocidal Host Range" Journal of Cellular Biochemistry, UCLA Symposia on Molecular & Cellular Biology, Mar. 31–Apr. 22, 1990, p. 341, abstract no. R436.

Gaertner, F. H., L. Kim (1988) "Current Applied Recombinant DNA Projects" TIBTECH 6:S4–S7.

Gaertner, F. H. (1989) "Cellular delivery systems for insecticidal proteins: living and non–living microorganisms" in Controlled Deliver of Crop–Protection Agents, pp. 245–255.

Couch, T. L. (1980) "Mosquito Pathogenicity of *Bacillus thuringiensis* var. *israelensis*" Developments in Industrial Microbiology 22:61–76.

Beegle, C. C. (1978) "Use of Entomogenous Bacteria in AGroecosystems" in Developments in Industrial Microbiology 20:97–104.

Krieg, A. et al. (1983) "*Bacillus thuringiensis* var. *tenebrionis*: ein neuer, gegenuber Larven von Coleopteren Wirksamer Pathotyp" Z. ang. Ent. 96:500–508.

Hofte, H., H. R. Whiteley (1989) "Insecticidal Crystal Proteins of *Bacillus thuringiensis*" Microbiological Reviews 52(2):242–255.

Feitelson, J. S. et al. (1992) "*Bacillus thuringiensis*: Insects and Beyond" Bio/Technology 10:271–275.

(List continued on next page.)

*Primary Examiner*—David Guzo
*Attorney, Agent, or Firm*—Saliwanchik & Saliwanchik

[57] ABSTRACT

An improved *Bacillus thuringiensis* (B.t.) delta-endotoxin is created by the modification of the gene encoding the toxin. The toxicity of a B.t. toxin was improved by replacing the native protoxin segment with an alternate protoxin segment by constructing a chimeric toxin gene.

7 Claims, 5 Drawing Sheets

OTHER PUBLICATIONS

Schnepf, H. E., H. R. Whiteley (1981) "Cloning and expression of the *Bacillus thuringiensis* crystal protein gene in *Escherichia coli*" Proc. Natl. Acad. Sci. USA 78(5):2893–2897.

Li, J., J. Carroll, D. J. Ellar (1991) "Crystal structure of insecticidal δ–endotoxin from *Bacillus thuringiensis* at 2.5 Å resolution" Nature 353:815–821.

Arvidson, H. et al. (1989) "Specificity of *Bacillus thuringiensis* for lepidopteran larvae: factors involved in vivo and in the structure of a purified protoxin" Molecular Microbiology 3(11):1533–1543.

Choma, C. T. et al. (1990) "Unusual proteolysis of the protoxin and toxin from *Bacillus thuringiensis*" Eur. J. Biochem. 189:523–527.

Haider, M. Z., et al. (1986) "Specificity of *Bacillus thuringiensis* var. *colmeri* insecticidal δ–endotoxin is determined by differential proteolytic processing of the protoxin" Eur. J. Biochem. 156:531–540.

Aronson, A. I. et al. (1991) "The Solubility of Inclusion Proteins from *Bacillus thuringiensis* Is Dependent upon Protoxin Composition and Is a Factor in Toxicity to Insects" Appl. Environ. Microbiol. 57(4):981–986.

Honee, G. et al. (1991) "The C-terminal domain of the toxic fragment of a *Bacillus thuringiensis* crystal protein determines receptor binding" *Molecular Microbiology* 5(11):2799–2806.

Honee, G. et al. (1990) "A Translation Fusion Product of Two Different Insecticidal Crystal Protein Genes of *Bacillus thuringiensis* Exhibits an Enlarged Insecticidal Spectrum" Appl. Environ. Microbiol. 56(3):823–825.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 39 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

GCATACTAGT AGGAGATTTC CATGGATAAC AATCCGAAC 39

( 2 ) INFORMATION FOR SEQ ID NO:2:

( i ) SEQUENCE CHARACTERISTICS:
( A ) LENGTH: 18 bases
( B ) TYPE: nucleic acid ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGATCCGCTT CCCAGTCT                                                                                                18

( 2 ) INFORMATION FOR SEQ ID NO:3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

AGAGAGTGGG AAGCGGATCC TACTAATCC                                                                                    29

( 2 ) INFORMATION FOR SEQ ID NO:4:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TGGATACTCG ATCGATATGA TAATCCGT                                                                                     28

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

TAATAAGAGC TCCTATGT                                                                                                18

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

TATCATATCG ATCGAGTATC CAATTTAG                                                                                     28

( 2 ) INFORMATION FOR SEQ ID NO:7:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

GTCACATAGC CAGCTGGT    18

( 2 ) INFORMATION FOR SEQ ID NO:8:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GAGTGGGAAG CAGATCTTAA TAATGCACAA TTAAGG    36

( 2 ) INFORMATION FOR SEQ ID NO:9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

TTAATCATCG GCTCGTA    17

( 2 ) INFORMATION FOR SEQ ID NO:10:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

ACTCGATCGA TATGATARTC CGT    23

( 2 ) INFORMATION FOR SEQ ID NO:11:

( i ) SEQUENCE CHARACTERISTICS:
        ( A ) LENGTH: 1163 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
             20                  25                  30

Ser Ser Ile Asp Ile Ser Leu Ser Leu Val Gln Phe Leu Val Ser Asn
         35                  40                  45

Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                 85                  90                  95
```

-continued

| | | | | | | | | | | | | | | |
|---|---|---|---|---|---|---|---|---|---|---|---|---|---|---|
| Ala | Asn | Leu | Glu 100 | Gly | Leu | Gly | Asn | Asn 105 | Phe | Asn | Ile | Tyr 110 | Val | Glu | Ala |
| Phe | Lys | Glu 115 | Trp | Glu | Glu | Asp | Pro 120 | Asn | Asn | Pro | Ala | Thr 125 | Arg | Thr | Arg |
| Val | Ile 130 | Asp | Arg | Phe | Arg | Ile 135 | Leu | Asp | Gly | Leu | Leu 140 | Glu | Arg | Asp | Ile |
| Pro 145 | Ser | Phe | Arg | Ile | Ser 150 | Gly | Phe | Glu | Val | Pro 155 | Leu | Leu | Ser | Val | Tyr 160 |
| Ala | Gln | Ala | Ala | Asn 165 | Leu | His | Leu | Ala | Ile 170 | Leu | Arg | Asp | Ser | Val 175 | Ile |
| Phe | Gly | Glu | Arg 180 | Trp | Gly | Leu | Thr | Thr 185 | Ile | Asn | Val | Asn | Glu 190 | Asn | Tyr |
| Asn | Arg | Leu 195 | Ile | Arg | His | Ile | Asp 200 | Glu | Tyr | Ala | Asp | His 205 | Cys | Ala | Asn |
| Thr | Tyr 210 | Asn | Arg | Gly | Leu | Asn 215 | Asn | Leu | Pro | Lys | Ser 220 | Thr | Tyr | Gln | Asp |
| Trp 225 | Ile | Thr | Tyr | Asn | Arg 230 | Leu | Arg | Arg | Asp | Leu 235 | Thr | Leu | Thr | Val | Leu 240 |
| Asp | Ile | Ala | Ala | Phe 245 | Phe | Pro | Asn | Tyr | Asp 250 | Asn | Arg | Arg | Tyr | Pro 255 | Ile |
| Gln | Pro | Val | Gly 260 | Gln | Leu | Thr | Arg | Glu 265 | Val | Tyr | Thr | Asp | Pro 270 | Leu | Ile |
| Asn | Phe | Asn 275 | Pro | Gln | Leu | Gln | Ser 280 | Val | Ala | Gln | Leu | Pro 285 | Thr | Phe | Asn |
| Val | Met 290 | Glu | Ser | Ser | Ala | Ile 295 | Arg | Asn | Pro | His | Leu 300 | Phe | Asp | Ile | Leu |
| Asn 305 | Asn | Leu | Thr | Ile | Phe 310 | Thr | Asp | Trp | Phe | Ser 315 | Val | Gly | Arg | Asn | Phe 320 |
| Tyr | Trp | Gly | Gly | His 325 | Arg | Val | Ile | Ser | Ser 330 | Leu | Ile | Gly | Gly | Gly 335 | Asn |
| Ile | Thr | Ser | Pro 340 | Ile | Tyr | Gly | Arg | Glu 345 | Ala | Asn | Gln | Glu | Pro 350 | Pro | Arg |
| Ser | Phe | Thr 355 | Phe | Asn | Gly | Pro | Val 360 | Phe | Arg | Thr | Leu | Ser 365 | Asn | Pro | Thr |
| Leu | Arg 370 | Leu | Leu | Gln | Gln | Pro 375 | Trp | Pro | Ala | Pro | Pro 380 | Phe | Asn | Leu | Arg |
| Gly 385 | Val | Glu | Gly | Val | Glu 390 | Phe | Ser | Thr | Pro | Thr 395 | Asn | Ser | Phe | Thr | Tyr 400 |
| Arg | Gly | Arg | Gly | Thr 405 | Val | Asp | Ser | Leu | Thr 410 | Glu | Leu | Pro | Pro | Glu 415 | Asp |
| Asn | Ser | Val | Pro 420 | Pro | Arg | Glu | Gly | Tyr 425 | Ser | His | Arg | Leu | Cys 430 | His | Ala |
| Thr | Phe | Val 435 | Gln | Arg | Ser | Gly | Thr 440 | Pro | Phe | Leu | Thr | Thr 445 | Gly | Val | Val |
| Phe | Ser 450 | Trp | Thr | His | Arg | Ser 455 | Ala | Thr | Leu | Thr | Asn 460 | Thr | Ile | Asp | Pro |
| Glu 465 | Arg | Ile | Asn | Gln | Ile 470 | Pro | Leu | Val | Lys | Gly 475 | Phe | Arg | Val | Trp | Gly 480 |
| Gly | Thr | Ser | Val | Ile 485 | Thr | Gly | Pro | Gly | Phe 490 | Thr | Gly | Gly | Asp | Ile 495 | Leu |
| Arg | Arg | Asn | Thr 500 | Phe | Gly | Asp | Phe | Val 505 | Ser | Leu | Gln | Val | Asn 510 | Ile | Asn |
| Ser | Pro | Ile 515 | Thr | Gln | Arg | Tyr | Arg 520 | Leu | Arg | Phe | Arg | Tyr 525 | Ala | Ser | Ser |

```
Arg  Asp  Ala  Arg  Val  Ile  Val  Leu  Thr  Gly  Ala  Ala  Ser  Thr  Gly  Val
     530                 535                      540

Gly  Gly  Gln  Val  Ser  Val  Asn  Met  Pro  Leu  Gln  Lys  Thr  Met  Glu  Ile
545                      550                      555                      560

Gly  Glu  Asn  Leu  Thr  Ser  Arg  Thr  Phe  Arg  Tyr  Thr  Asp  Phe  Ser  Asn
                    565                      570                      575

Pro  Phe  Ser  Phe  Arg  Ala  Asn  Pro  Asp  Ile  Ile  Gly  Ile  Ser  Glu  Gln
               580                      585                      590

Pro  Leu  Phe  Gly  Ala  Gly  Ser  Ile  Ser  Ser  Gly  Glu  Leu  Tyr  Ile  Asp
          595                      600                      605

Lys  Ile  Glu  Ile  Ile  Leu  Ala  Asp  Ala  Thr  Phe  Glu  Ala  Glu  Ser  Asp
     610                      615                      620

Leu  Glu  Arg  Ala  Gln  Lys  Ala  Val  Asn  Ala  Leu  Phe  Thr  Ser  Ser  Asn
625                      630                      635                      640

Gln  Ile  Gly  Leu  Lys  Thr  Asp  Val  Thr  Asp  Tyr  His  Ile  Asp  Arg  Val
                    645                      650                      655

Ser  Asn  Leu  Val  Glu  Cys  Leu  Ser  Asp  Glu  Phe  Cys  Leu  Asp  Glu  Lys
               660                      665                      670

Lys  Glu  Leu  Ser  Glu  Lys  Val  Lys  His  Ala  Lys  Arg  Leu  Ser  Asp  Glu
          675                      680                      685

Arg  Asn  Leu  Leu  Gln  Asp  Pro  Asn  Phe  Arg  Gly  Ile  Asn  Arg  Gln  Leu
     690                      695                      700

Asp  Arg  Gly  Trp  Arg  Gly  Ser  Thr  Asp  Ile  Thr  Ile  Gln  Gly  Gly  Asp
705                      710                      715                      720

Asp  Val  Phe  Lys  Glu  Asn  Tyr  Val  Thr  Leu  Leu  Gly  Thr  Phe  Asp  Glu
                    725                      730                      735

Cys  Tyr  Pro  Thr  Tyr  Leu  Tyr  Gln  Lys  Ile  Asp  Glu  Ser  Lys  Leu  Lys
               740                      745                      750

Ala  Tyr  Thr  Arg  Tyr  Gln  Leu  Arg  Gly  Tyr  Ile  Glu  Asp  Ser  Gln  Asp
          755                      760                      765

Leu  Glu  Ile  Tyr  Leu  Ile  Arg  Tyr  Asn  Ala  Lys  His  Glu  Thr  Val  Asn
     770                      775                      780

Val  Pro  Gly  Thr  Gly  Ser  Leu  Trp  Pro  Leu  Ser  Ala  Pro  Ser  Pro  Ile
785                      790                      795                      800

Gly  Lys  Cys  Ala  His  His  Ser  His  His  Phe  Ser  Leu  Asp  Ile  Asp  Val
                    805                      810                      815

Gly  Cys  Thr  Asp  Leu  Asn  Glu  Asp  Leu  Gly  Val  Trp  Val  Ile  Phe  Lys
               820                      825                      830

Ile  Lys  Thr  Gln  Asp  Gly  His  Ala  Arg  Leu  Gly  Asn  Leu  Glu  Phe  Leu
          835                      840                      845

Glu  Glu  Lys  Pro  Leu  Val  Gly  Glu  Ala  Leu  Ala  Arg  Val  Lys  Arg  Ala
850                      855                      860

Glu  Lys  Lys  Trp  Arg  Asp  Lys  Arg  Glu  Lys  Leu  Glu  Trp  Glu  Thr  Asn
865                      870                      875                      880

Ile  Val  Tyr  Lys  Glu  Ala  Lys  Glu  Ser  Val  Asp  Ala  Leu  Phe  Val  Asn
                    885                      890                      895

Ser  Gln  Tyr  Asp  Arg  Leu  Gln  Ala  Asp  Thr  Asn  Ile  Ala  Met  Ile  His
               900                      905                      910

Ala  Ala  Asp  Lys  Arg  Val  His  Ser  Ile  Arg  Glu  Ala  Tyr  Leu  Pro  Glu
          915                      920                      925

Leu  Ser  Val  Ile  Pro  Gly  Val  Asn  Ala  Ala  Ile  Phe  Glu  Glu  Leu  Glu
     930                      935                      940

Gly  Arg  Ile  Phe  Thr  Ala  Phe  Ser  Leu  Tyr  Asp  Ala  Arg  Asn  Val  Ile
```

```
                 945                            950                          955                        960
    Lys  Asn  Gly  Asp  Phe  Asn  Asn  Gly  Leu  Ser  Cys  Trp  Asn  Val  Lys  Gly
                        965                           970                        975

His  Val  Asp  Val  Glu  Glu  Gln  Asn  Asn  His  Arg  Ser  Val  Leu  Val  Val
                   980                           985                    990

Pro  Glu  Trp  Glu  Ala  Glu  Val  Ser  Gln  Glu  Val  Arg  Val  Cys  Pro  Gly
                   995                          1000                   1005

Arg  Gly  Tyr  Ile  Leu  Arg  Val  Thr  Ala  Tyr  Lys  Glu  Gly  Tyr  Gly  Glu
             1010                       1015                       1020

Gly  Cys  Val  Thr  Ile  His  Glu  Ile  Glu  Asn  Asn  Thr  Asp  Glu  Leu  Lys
    1025                       1030                       1035                    1040

Phe  Ser  Asn  Cys  Val  Glu  Glu  Val  Tyr  Pro  Asn  Asn  Thr  Val  Thr
                        1045                      1050                      1055

Cys  Asn  Asp  Tyr  Thr  Ala  Thr  Gln  Glu  Glu  Tyr  Glu  Gly  Thr  Tyr  Thr
                   1060                      1065                      1070

Ser  Arg  Asn  Arg  Gly  Tyr  Asp  Gly  Ala  Tyr  Glu  Ser  Asn  Ser  Ser  Val
                   1075                      1080                      1085

Pro  Ala  Asp  Tyr  Ala  Ser  Ala  Tyr  Glu  Glu  Lys  Ala  Tyr  Thr  Asp  Gly
              1090                      1095                       1100

Arg  Arg  Asp  Asn  Pro  Cys  Glu  Ser  Asn  Arg  Gly  Tyr  Gly  Asp  Tyr  Thr
    1105                       1110                       1115                    1120

Pro  Leu  Pro  Ala  Gly  Tyr  Val  Thr  Lys  Glu  Leu  Glu  Tyr  Phe  Pro  Glu
                        1125                      1130                      1135

Thr  Asp  Lys  Val  Trp  Ile  Glu  Ile  Gly  Glu  Thr  Glu  Gly  Thr  Phe  Ile
                   1140                      1145                      1150

Val  Asp  Ser  Val  Glu  Leu  Leu  Leu  Met  Glu  Glu
                   1155                      1160
```

( 2 ) INFORMATION FOR SEQ ID NO:12:

( i ) SEQUENCE CHARACTERISTICS:
        ( A ) LENGTH: 1190 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
    Met  Glu  Glu  Asn  Asn  Gln  Asn  Gln  Cys  Ile  Pro  Tyr  Asn  Cys  Leu  Ser
    1                   5                        10                       15

Asn  Pro  Glu  Glu  Val  Leu  Leu  Asp  Gly  Glu  Arg  Ile  Ser  Thr  Gly  Asn
                   20                       25                       30

Ser  Ser  Ile  Asp  Ile  Ser  Leu  Ser  Leu  Val  Gln  Phe  Leu  Val  Ser  Asn
              35                       40                       45

Phe  Val  Pro  Gly  Gly  Gly  Phe  Leu  Val  Gly  Leu  Ile  Asp  Phe  Val  Trp
         50                       55                       60

Gly  Ile  Val  Gly  Pro  Ser  Gln  Trp  Asp  Ala  Phe  Leu  Val  Gln  Ile  Glu
    65                       70                       75                       80

Gln  Leu  Ile  Asn  Glu  Arg  Ile  Ala  Glu  Phe  Ala  Arg  Asn  Ala  Ala  Ile
                        85                       90                       95

Ala  Asn  Leu  Glu  Gly  Leu  Gly  Asn  Asn  Phe  Asn  Ile  Tyr  Val  Glu  Ala
                   100                      105                      110

Phe  Lys  Glu  Trp  Glu  Glu  Asp  Pro  Xaa  Asn  Pro  Xaa  Thr  Arg  Thr  Arg
              115                      120                      125

Val  Ile  Asp  Arg  Phe  Arg  Ile  Leu  Asp  Gly  Leu  Leu  Glu  Arg  Asp  Ile
    130                      135                      140
```

```
Pro  Ser  Phe  Arg  Ile  Ser  Gly  Phe  Glu  Val  Pro  Leu  Leu  Ser  Val  Tyr
145            150                     155                           160

Ala  Gln  Ala  Ala  Asn  Leu  His  Leu  Ala  Ile  Leu  Arg  Asp  Ser  Val  Ile
               165                     170                      175

Phe  Gly  Glu  Arg  Trp  Gly  Leu  Thr  Thr  Ile  Asn  Val  Asn  Glu  Asn  Tyr
          180                     185                      190

Asn  Arg  Leu  Ile  Arg  His  Ile  Asp  Glu  Tyr  Ala  Asp  His  Cys  Ala  Asn
          195                200                           205

Thr  Tyr  Asn  Arg  Gly  Leu  Asn  Asn  Leu  Pro  Lys  Ser  Thr  Tyr  Gln  Asp
          210                     215                      220

Trp  Ile  Thr  Tyr  Asn  Arg  Leu  Arg  Arg  Asp  Leu  Thr  Leu  Thr  Val  Leu
225                      230                     235                          240

Asp  Ile  Ala  Ala  Phe  Phe  Pro  Asn  Tyr  Asp  Asn  Arg  Arg  Tyr  Pro  Ile
               245                     250                          255

Gln  Pro  Val  Gly  Gln  Leu  Thr  Arg  Glu  Val  Tyr  Thr  Asp  Pro  Leu  Ile
               260                     265                      270

Asn  Phe  Asn  Pro  Gln  Leu  Gln  Ser  Val  Ala  Gln  Leu  Pro  Thr  Phe  Asn
          275                     280                      285

Val  Met  Glu  Ser  Ser  Xaa  Ile  Arg  Asn  Pro  His  Leu  Phe  Asp  Ile  Leu
     290                295                           300

Asn  Asn  Leu  Thr  Ile  Phe  Thr  Asp  Trp  Phe  Ser  Val  Gly  Arg  Asn  Phe
305                      310                     315                          320

Tyr  Trp  Gly  Gly  His  Arg  Val  Ile  Ser  Ser  Leu  Ile  Gly  Gly  Gly  Asn
               325                     330                          335

Ile  Thr  Ser  Pro  Ile  Tyr  Gly  Arg  Glu  Ala  Asn  Gln  Glu  Pro  Pro  Arg
               340                     345                      350

Ser  Phe  Thr  Phe  Asn  Gly  Pro  Val  Phe  Arg  Thr  Leu  Ser  Xaa  Pro  Thr
          355                     360                      365

Leu  Arg  Leu  Leu  Gln  Gln  Pro  Xaa  Xaa  Xaa  Xaa  Phe  Asn  Leu  Arg
     370                     375                      380

Gly  Xaa  Glu  Gly  Val  Glu  Phe  Ser  Thr  Pro  Thr  Asn  Ser  Phe  Thr  Tyr
385                      390                     395                          400

Arg  Gly  Arg  Gly  Xaa  Val  Asp  Ser  Leu  Thr  Glu  Leu  Pro  Pro  Glu  Asp
               405                     410                           415

Asn  Ser  Val  Pro  Pro  Arg  Glu  Gly  Tyr  Ser  His  Arg  Leu  Cys  His  Ala
               420                     425                      430

Thr  Phe  Val  Gln  Arg  Ser  Gly  Thr  Pro  Phe  Leu  Thr  Thr  Gly  Val  Val
          435                     440                      445

Phe  Ser  Trp  Thr  Xaa  Arg  Ser  Ala  Thr  Leu  Thr  Asn  Thr  Ile  Asp  Pro
     450                     455                      460

Glu  Arg  Ile  Asn  Gln  Ile  Pro  Leu  Val  Lys  Gly  Phe  Arg  Val  Trp  Gly
465                      470                     475                          480

Gly  Thr  Ser  Val  Ile  Thr  Gly  Pro  Gly  Phe  Thr  Gly  Gly  Asp  Ile  Leu
               485                     490                          495

Arg  Arg  Asn  Thr  Phe  Gly  Asp  Phe  Val  Ser  Leu  Gln  Val  Asn  Ile  Asn
               500                     505                      510

Ser  Pro  Ile  Thr  Gln  Arg  Tyr  Arg  Leu  Arg  Phe  Arg  Tyr  Ala  Ser  Ser
          515                     520                      525

Arg  Asp  Ala  Arg  Val  Ile  Val  Leu  Thr  Gly  Ala  Ala  Ser  Thr  Gly  Val
     530                     535                      540

Gly  Gly  Gln  Val  Ser  Val  Asn  Met  Pro  Leu  Gln  Lys  Thr  Met  Glu  Ile
545                      550                     555                          560

Gly  Glu  Asn  Leu  Thr  Ser  Arg  Thr  Phe  Arg  Tyr  Thr  Asp  Phe  Ser  Asn
```

|     |     |     |     | 565 |     |     |     | 570 |     |     |     | 575 |     |     |
| --- | --- | --- | --- | --- | --- | --- | --- | --- | --- | --- | --- | --- | --- | --- |
| Pro | Phe | Ser | Phe<br>580 | Arg | Ala | Asn | Pro<br>585 | Ile | Ile | Gly | Ile<br>590 | Ser | Glu | Gln |
| Pro | Leu | Phe<br>595 | Gly | Ala | Gly | Ser<br>600 | Ile | Ser | Gly | Glu | Leu<br>605 | Tyr | Ile | Asp |
| Lys | Ile<br>610 | Glu | Ile | Ile | Leu<br>615 | Ala | Asp | Ala | Thr | Phe<br>620 | Glu | Ala | Glu | Ser | Asp |
| Leu<br>625 | Glu | Arg | Ala | Gln | Lys<br>630 | Ala | Val | Asn | Xaa | Leu<br>635 | Phe | Thr | Ser | Xaa | Asn<br>640 |
| Gln | Ile | Gly | Leu | Lys<br>645 | Thr | Asp | Val | Thr | Asp<br>650 | Tyr | His | Ile | Asp | Gln<br>655 | Val |
| Ser | Asn | Leu | Val<br>660 | Glu | Cys | Leu | Ser | Asp<br>665 | Glu | Phe | Cys | Leu | Asp<br>670 | Glu | Lys |
| Xaa | Glu | Leu<br>675 | Ser | Glu | Lys | Val | Lys<br>680 | His | Ala | Xaa | Xaa | Leu<br>685 | Ser | Asp | Glu |
| Arg | Asn<br>690 | Leu | Leu | Gln | Asp | Pro<br>695 | Asn | Phe | Arg | Gly | Ile<br>700 | Asn | Arg | Gln | Xaa |
| Asp<br>705 | Arg | Gly | Trp | Arg | Gly<br>710 | Ser | Thr | Asp | Ile | Thr<br>715 | Ile | Gln | Gly | Gly | Asp<br>720 |
| Asp | Val | Phe | Lys | Glu<br>725 | Asn | Tyr | Val | Thr | Leu<br>730 | Xaa | Gly | Thr | Phe<br>735 | Asp | Glu |
| Cys | Tyr | Xaa | Thr<br>740 | Tyr | Leu | Tyr | Gln | Lys<br>745 | Ile | Asp | Glu | Ser | Lys<br>750 | Leu | Lys |
| Ala | Tyr | Thr<br>755 | Arg | Tyr | Xaa | Leu | Arg<br>760 | Gly | Tyr | Ile | Glu | Asp<br>765 | Ser | Gln | Asp |
| Leu | Glu<br>770 | Ile | Tyr | Leu | Ile | Arg<br>775 | Tyr | Asn | Ala | Lys | His<br>780 | Glu | Thr | Val | Asn |
| Val<br>785 | Pro | Gly | Thr | Gly | Ser<br>790 | Leu | Trp | Xaa | Leu | Ser<br>795 | Xaa | Xaa | Ser | Ser | Ile<br>800 |
| Gly | Xaa | Xaa | Xaa | Xaa<br>805 | Xaa | Xaa | Xaa | Xaa | Xaa<br>810 | Xaa | Xaa | Xaa | Xaa | Xaa<br>815 | Xaa |
| Xaa | Xaa | Xaa | Xaa<br>820 | Xaa | Xaa | Xaa | Xaa | Xaa<br>825 | Xaa | Xaa | Lys | Cys | Ala<br>830 | His | His |
| Ser | His | His<br>835 | Phe | Ser | Leu | Asp | Ile<br>840 | Asp | Val | Gly | Cys | Xaa<br>845 | Asp | Leu | Asn |
| Glu | Asp<br>850 | Leu | Gly | Val | Trp | Val<br>855 | Ile | Phe | Lys | Ile | Lys<br>860 | Thr | Gln | Asp | Gly |
| His<br>865 | Xaa | Arg | Leu | Gly | Xaa<br>870 | Leu | Glu | Phe | Leu | Glu<br>875 | Xaa | Xaa | Xaa | Pro | Leu<br>880 |
| Val | Gly | Glu | Ala | Leu<br>885 | Ala | Arg | Val | Lys | Arg<br>890 | Ala | Glu | Lys | Lys | Trp<br>895 | Arg |
| Asp | Lys | Arg | Glu<br>900 | Lys | Leu | Xaa | Xaa | Glu<br>905 | Thr | Asn | Ile | Val | Tyr<br>910 | Lys | Glu |
| Ala | Lys | Glu<br>915 | Ser | Val | Asp | Ala | Leu<br>920 | Phe | Val | Asn | Ser | Gln<br>925 | Tyr | Asp | Xaa |
| Leu | Gln<br>930 | Ala | Asp | Thr | Asn | Ile<br>935 | Ala | Met | Ile | His | Xaa<br>940 | Ala | Asp | Lys | Arg |
| Val<br>945 | His | Xaa | Ile | Xaa | Glu<br>950 | Ala | Tyr | Leu | Pro | Glu<br>955 | Leu | Ser | Val | Ile | Pro<br>960 |
| Gly | Val | Asn | Ala | Xaa<br>965 | Ile | Phe | Glu | Glu | Leu<br>970 | Glu | Gly | Arg | Ile | Phe<br>975 | Thr |
| Ala | Phe | Ser | Leu<br>980 | Tyr | Asp | Ala | Arg | Asn<br>985 | Val | Ile | Lys | Asn | Gly<br>990 | Asp | Phe |

```
Asn  Asn  Gly  Leu  Ser  Cys  Trp  Asn  Val  Lys  Gly  His  Val  Asp  Val  Glu
          995                      1000                     1005

Glu  Gln  Asn  Asn  Xaa  Arg  Ser  Val  Leu  Val  Val  Pro  Glu  Trp  Glu  Ala
     1010                      1015                     1020

Glu  Val  Ser  Gln  Glu  Val  Arg  Val  Cys  Pro  Gly  Arg  Gly  Tyr  Ile  Leu
1025                     1030                     1035                     1040

Arg  Val  Thr  Ala  Tyr  Lys  Glu  Gly  Tyr  Gly  Xaa  Gly  Cys  Val  Thr  Ile
                    1045                     1050                     1055

His  Glu  Ile  Glu  Asn  Asn  Thr  Asp  Glu  Leu  Lys  Phe  Ser  Asn  Xaa  Val
               1060                     1065                     1070

Glu  Glu  Glu  Val  Tyr  Pro  Asn  Asn  Thr  Val  Thr  Cys  Asn  Asp  Tyr  Thr
          1075                     1080                     1085

Ala  Xaa  Gln  Glu  Glu  Tyr  Xaa  Gly  Xaa  Tyr  Thr  Ser  Xaa  Asn  Arg  Gly
     1090                     1095                     1100

Tyr  Asp  Xaa  Xaa  Tyr  Xaa  Ser  Asn  Xaa  Ser  Val  Pro  Ala  Asp  Tyr  Ala
1105                     1110                     1115                     1120

Ser  Xaa  Tyr  Glu  Glu  Lys  Ala  Tyr  Thr  Asp  Gly  Arg  Arg  Asp  Asn  Pro
               1125                     1130                     1135

Cys  Glu  Ser  Asn  Arg  Gly  Tyr  Gly  Asp  Tyr  Thr  Pro  Leu  Pro  Ala  Gly
               1140                     1145                     1150

Tyr  Val  Thr  Lys  Xaa  Leu  Glu  Tyr  Phe  Pro  Glu  Thr  Asp  Lys  Val  Trp
          1155                     1160                     1165

Ile  Glu  Ile  Gly  Glu  Thr  Glu  Gly  Thr  Phe  Ile  Val  Asp  Ser  Val  Glu
     1170                     1175                     1180

Leu  Leu  Leu  Met  Glu  Glu
1185                1190
```

( 2 ) INFORMATION FOR SEQ ID NO:13:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:13:

```
Xaa  Xaa  Ile  Asp  Xaa  Xaa  Glu  Xaa  Xaa  Xaa  Xaa  Xaa
                    5                        10
```

BACILLUS THURINGIENSIS DELTA-ENDOTOXIN

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4–S7). Thus, isolated B.t. endotoxin genes are becoming commercially valuable.

Until the last ten years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *tenebrionis* (a.k.a.B.t. M-7, a.k.a.B.t. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) Z. *ang. Ent.* 96:500–508, describe *Bacillus thuringiensis* var. *tenebdonis*, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for encoding active δ-endotoxin proteins have been isolated (Höfte, H., H. R. Whiteley [1989] *Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992]*Bio/Technology* 10:271–275).

The cloning and expression of a B.t. crystal protein gene in *Escherichia coli* has been described in the published literature (Schnepf, H. E., H. R. Whiteley [1981] *Proc. Natl. Acad. Sci. U.S.A.* 78:2893–2897). U.S. Pat. No. 4,448,885 and U.S. Pat. No. 4,467,036 both disclose the expression of B.t. crystal protein in *E. coli*. Hybrid B.t. crystal proteins have been constructed that exhibit increased toxicity and display an expanded host range to a target pest. See U.S. Pat. Nos. 5,238,130 and 5,055,294. U.S. Pat. Nos. 4,797,276 and 4,853,331 disclose *B. thuringiensis* strain *tenebrionis* (a.k.a. M-7, a.k.a.B.t. *san diego*) which can be used to control coleopteran pests in various environments. U.S. Pat. No. 4,918,006 discloses B.t. toxins having activity against dipterans. U.S. Pat. No. 4,849,217 discloses B.t. isolates which have activity against the alfalfa weevil. U.S. Pat. No. 5,208,077 discloses coleopteran-active *Bacillus thuringiensis* isolates. U.S. Pat. No. 5,151,363 and U.S. Pat. No. 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

A majority of *Bacillus thuringiensis* δ-endotoxin crystal protein molecules are composed of two functional segments. The protease-resistant core toxin is the first segment and corresponds to about the first haft of the protein molecule. The three-dimensional structure of a core segment of a cryIIIA B.t. δ-endotoxin is known and it is proposed that all related toxins have that same overall structure (Li, J., J. Carroll, D. J. Ellar [1991] *Nature* 353:815–821). The second half of the molecule is the second segment. For purposes of this application, this second segment will be referred to herein as the "protoxin segment." The protoxin segment is believed to participate in toxin crystal formation (Arvidson, H., P. E. Dunn, S. Strand, A. I. Aronson [1989] *Molecular Microbiology* 3:1533–1534; Choma, C. T., W. K. Surewicz, P. R. Carey, M. Pozsgay, T. Raynor, H. Kaplan [1990] *Eur. J. Biochem.* 189:523–527). The full toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J. Biochem.* 156:531–540) or by reducing toxin solubility (Aronson, A. I., E. S. Han, W. McGaughey, D. Johnson [1991] *Appl. Environ. Microbiol.* 57:981–986).

Chimeric proteins joined within the toxin domains have been reported between CryIC and CryIA(b) (Honee, G., D. Convents, J. Van Rie, S. Jansens, M. Perferoen, B. Visser [1991] *Mol. Microbiol.* 5:2799–2806); however, the activity of these chimeric proteins was either much less, or undetectable, when compared to CryIC on a relevant insect.

Honee et al. (Honee, G., W. Vriezen, B. Visser [1990] *Appl. Environ. Microbiol.* 56:823–825) also reported making a chimeric fusion protein by linking tandem toxin domains of CryIC and CryIA(b). The resulting protein had an increased spectrum of activity equivalent to the combined activities of the individual toxins; however, the activity of the chimeric was not increased toward any one of the target insects.

BRIEF SUMMARY OF THE INVENTION

The subject invention concerns the discovery that the activity of a *Bacillus thuringiensis* (B.t.) δ-endotoxin can be substantially improved by replacing native protoxin amino acids with an alternate protoxin sequence, yielding a chimeric toxin. In a specific embodiment of the subject invention, a chimeric toxin is assembled by substituting all or part of the cryIA(b) protoxin segment for all or part of the native cryIC protoxin segment. The cryIC/cryIA(b) chimeric toxin demonstrates an increased toxicity over the cryIC/cryIC toxin produced by the native gene.

One aspect of the subject invention pertains to genes which encode the advantageous chimeric toxins. Specifically exemplified is a gene comprising DNA encoding the cryIC core N-terminal toxin portion of the chimeric toxin and the cryIA(b) C-terminal protoxin portion of the toxin.

The subject invention further pertains to the use of the chimeric toxin, or microbes containing the gene encoding the chimeric toxin, in methods for controlling lepidopteran pests. The subject invention also includes use of the chimeric gene encoding the claimed toxin. The chimeric gene can be introduced into a wide variety of microbial or plant hosts. A transformed host expressing the chimeric gene can be used to produce the lepidopteran-active toxin of the subject invention. Transformed hosts can be used to produce the insecticidal toxin or, in the case of a plant cell transformed to produce the toxin, the plant will become resistant to insect attack.

Still further, the invention includes the treatment of substantially intact recombinant cells producing the chimeric toxin of the invention. The cells are treated to prolong the lepidopteran activity when the substantially intact cells are applied to the environment of a target pest. Such treatment can be by chemical or physical means, or a combination of chemical and physical means, so long as the chosen means do not deleteriously affect the properties of the pesticide, nor diminish the cell's capability of protecting the pesticide. The treated cell acts as a protective coating for the pesticidal toxin. The toxin becomes active upon ingestion by a target insect.

BRIEF DESCRIPTION OF THE SEQUENCES

Figure 1:
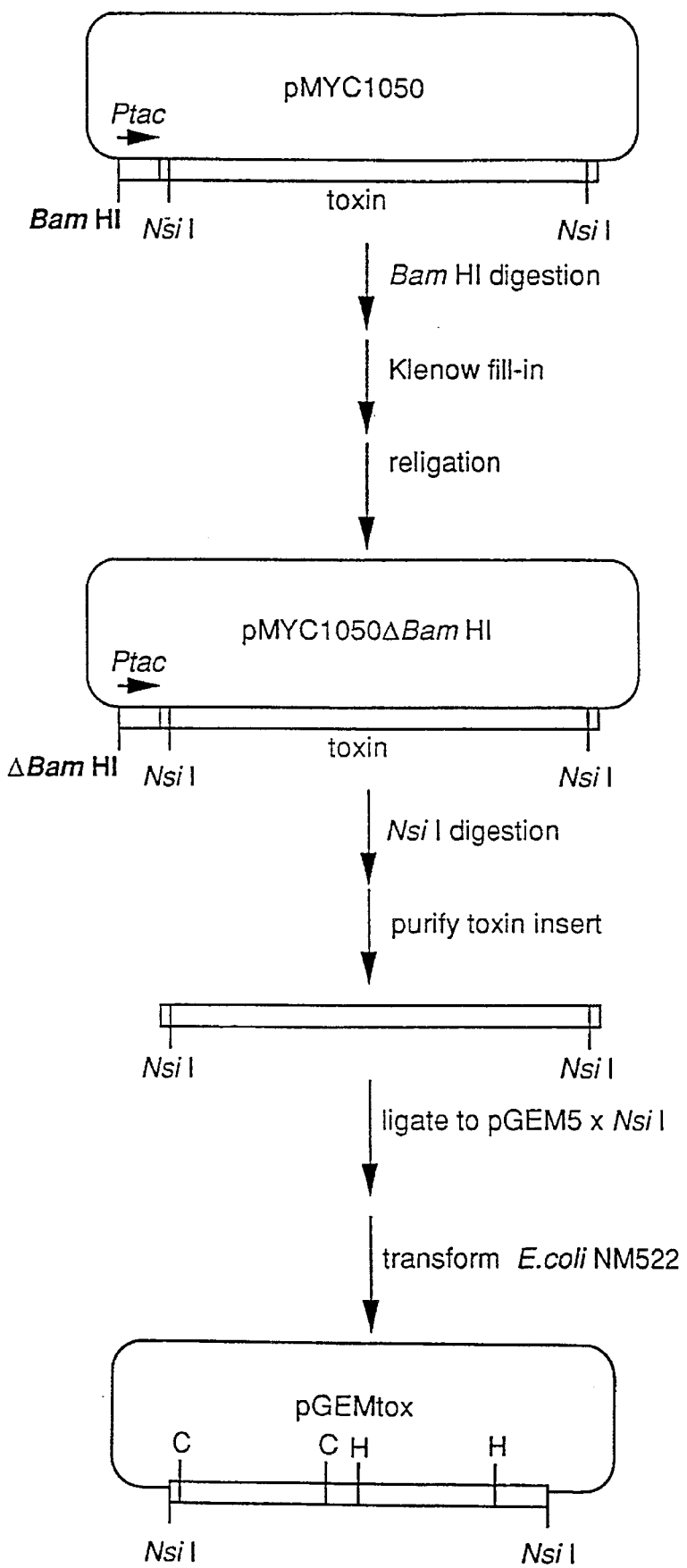
FIG. 1—The BamHI site is removed from pMYC1050 by a fill-in reaction with Klenow polymeruse to give plasmid pMYC1050ΔBamHI. To facilitate cloning, an NsiI DNA fragment that contains most of the toxin open reading frame is cloned into pGEM5. The resulting plasmid is called pGEMtox. C=ClaI, H=HindIII.

SEQ ID NO. 1 is oligonucleotide primer "A"
SEQ ID NO. 2 is oligonucleotide primer "B"
SEQ ID NO. 3 is oligonucleotide primer "C"
SEQ ID NO. 4 is oligonucleotide primer "D"
SEQ ID NO. 5 is oligonucleotide primer "E"
SEQ ID NO. 6 is oligonucleotide primer "F"
SEQ ID NO. 7 is oligonucleotide primer "G"
SEQ ID NO. 8 is oligonucleotide primer "L"
SEQ ID NO. 9 is oligonucleotide primer "N"
SEQ ID NO. 10 is oligonucleotide primer "O"
SEQ ID NO. 11 shows an amino acid sequence for a chimeric toxin of the subject invention.
SEQ ID NO. 12 shows an alternate amino acid sequence for a chimeric toxin of the subject invention.
SEQ ID NO. 13 is a characteristic sequence of cryI toxins. This sequence ends at residue 616 of SEQ ID NO. 11.

DETAILED DISCLOSURE OF THE INVENTION

The subject invention concerns the discovery of highly active chimeric *Bacillus thuringiensis* toxins. These chimeric toxins are created by replacing all or part of the native protoxin segment of a full length B.t. toxin with an alternate protoxin segment. In a preferred embodiment, the chimeric toxin comprises a cryIA(b) C-terminal protoxin portion and a cryIC core N-terminal toxin portion. As used herein, reference to a "core" toxin portion refers to the portion of the full length B.t. toxin, other than the protoxin, which is responsible for the pesticidal activity of the toxin.

*Bacillus thuringiensis* strains and other bacteria harboring plasmids useful according to the subject invention are the following:

| Culture | Repository No. | U.S. Pat. No. |
| --- | --- | --- |
| Bacillus thuringiensis strain PS81I | NRRL B-18484 | 5,273,746 |
| Escherichia coli NM522 (pMYC 394) | NRRL B-18500 | 5,126,133 |
| Pseudomonas fluorescens (pM3, 130-7) | NRRL B-18332 | 5,055,294 |
| Pseudomonas fluorescens MR436 (pM2, 16-11, aka pMYC436) | NRRL B-18292 | 5,128,130 |

It should be understood that the availability of a deposit does not constitute a license to practice the subject invention in derogation of patent rights granted by governmental action.

The flow charts of FIGS. 1–4 provide a general overview of vector construction that can be carried out according to the subject invention. BamHI and PvuI cloning sites were introduced into a cryIA(c)/cryIA(b) chimeric toxin gene by mutagenesis using the PCR technique of Splice Overlap Extension (SOE) (Horton, R. M., H. D. Hunt, S. N. Ho, J. K. Pullen, L. R. Pease [1989]*Gene* 77:61–68) to give plasmid pMYC2224. A region of the cryIC gene from a cryIC-containing plasmid such as pMYC394 can be generated by PCR and substituted for the BamHI-PvuI cryIA(c)/cryIA(b) gene fragment of pMYC2224. A plasmid created in this manner, pMYC2238, consisted of a short segment of cryIA(c) followed by cryIC to the toxin/protoxin segment junction. The protoxin segment was cryIA(b) from pMYC1050. Fragments of plasmid pMYC2238, plasmid pMYC1197, and a cryIC portion of plasmid pMYC394 were ligated to construct a chimeric gene encoding the toxin of the subject invention. The chimeric gene encodes the claimed toxin comprising a cryIC core N-terminal toxin portion and a cryIA(b) C-terminal protoxin portion which has increased lepidopteran activity compared to a native cryIC toxin.

The chimeric toxins of the subject invention comprise a full core N-terminal toxin portion of a B.t. toxin and, at some point past the end of the toxin portion, the protein has a transition to a heterologous protoxin sequence. The transition to the heterologous protoxin segment can occur at approximately the toxin/protoxin junction or, in the alternative, a portion of the native protoxin (extending past the toxin portion) can be retained with the transition to the heterologous protoxin occurring downstream. As an example, one chimeric toxin of the subject invention has the full toxin portion of cryIC (amino acids 1–616), a portion of the native cryIC protoxin (amino acids 617 to 655), and a heterologous portion of the protoxin (amino acids 656 to the C-terminus). In a preferred embodiment, the heterologous portion of the protoxin is derived from a cryIA(b) toxin.

A person skilled in this art will appreciate that B.t. toxins, even within a certain class such as cryIC, will vary to some extent in length and the precise location of the transition from toxin portion to protoxin portion. Typically, the cryIA(b) and cryIC toxins will be about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length B.t. toxin. This will typically be at least about 600 amino acids. With regard to the protoxin portion, the full expanse of the cryIA(b) protoxin portion extends from the end of the toxin portion to the C-terminus of the molecule. It is the last about 100 to 150 amino acids of this portion which are most critical to include in the chimeric toxin of the subject invention. In a chimeric toxin specifically exemplified herein, at least amino acids 1085 to the C-terminus of the cryIA(b) molecule are utilized. Thus, it is at least the last approximately 5 to 10% of the overall B.t. protein which should comprise heterologous DNA (compared to the cryIF core N-terminal toxin portion) included in the chimeric toxin of the subject invention. Thus, a preferred embodiment of the subject invention is a chimeric B.t. toxin of about 1150 to about 1200 amino acids in length, wherein the chimeric toxin comprises a cryIC core N-terminal toxin portion of at least about 50 to 60% of a full cryIC molecule, but no more than about 90 to 95% of the full molecule. The chimeric toxin further comprises a cryIA(b) protoxin C-terminal portion which comprises at least about 5 to 10% of the cryIA(b) molecule. The transition from cryIC to cryIA(b) sequence thus occurs within the protoxin segment (or at the junction of the toxin and protoxin segments) between about 50% and about 95% of the way through the molecule. In the specific example provided herein, the transition from the cryIC sequence to the cryIA(b) sequence occurs prior to amino acid 1085 of the chimeric toxin.

A specific embodiment of the subject invention is the chimeric toxin of SEQ ID NO. 11. Other constructs may be made and used by those skilled in this art having the benefit of the teachings provided herein. The core toxin segment of cryI proteins characteristically ends with the sequence: Val/Leu Tyr/Ile Ile Asp Arg/Lys Ile/Phe Glu Ile/Phe Ile/Leu/ Val Pro/Leu Ala/Val Glu/Thr/Asp (SEQ ID NO. 13), which ends at residue 616 of SEQ ID NO. 11. Additionally, the protoxin segments of the cryI toxins (following residue 616 of SEQ ID NO. 11) bear more sequence similarity than the toxin segments. Because of this sequence similarity, the transition point in the protoxin segment for making a chimeric protein between the cryIC sequence and the cryIA(b) sequence can be readily determined by one skilled in the art. From studies of data regarding the partial proteolysis of CryI genes, the heterogeneity and least-conserved amino acid regions are found after the conserved cryI protoxin sequence, positions 1077–1084 of SEQ ID NO. 12 (or 1050–1057 of SEQ ID NO. 11).

Therefore a chimeric toxin of the subject invention can comprise the full cryIC toxin and a portion of the cryIC protoxin, transitioning to the corresponding cryIA(b) sequence at any position between the end of the toxin segment (as defined above) and about position 1084. Preferably, the amino acids which correspond to positions 1085 through 1190 (SEQ ID NO. 12; 1058–1163 of SEQ ID NO. 11) comprise a cryIA(b) sequence or equivalent thereof.

CryIC toxins, and genes which encode these toxins, are well known in the art. CryIC genes and toxins have been described in, for example, U.S. Pat. No. 5,188,960 (gene designated 81IB2); Honee et al. (1988) *Nucleic Acids Res.* 16:6240; and Sanchis et al. (1988) *Mol. Microbiol.* 2:393. Also, various cryIA(b) toxins are well known in the art. CryIA(b) genes and toxins have been described in, for example, Höfte et al. (1986) *Eur. J. Biochem.* 161:273; Geiser et al. (1986) *Gene* 48:109; and Haider et al. (1988) *Nucleic Acids Res.* 16:10927. The skilled artisan having the benefit of the teachings contained herein could readily identify and use DNA which encodes the toxin N-terminal portion of a cryIC molecule and the C-terminal protoxin portion of the cryIA(b) toxins.

Positions where amino acid substitutions can be used in the toxins of the subject invention are shown in SEQ ID NO. 12. It is also well known in the art that various mutations can be made in a toxin sequence without changing the activity of a toxin. Furthermore, due to the degeneracy of the genetic code, a variety of DNA sequences can be used to encode a particular toxin. These alternative DNA and amino acid sequences can be used according to the subject invention by a person skilled in this art.

The protoxin substitution techniques of the subject invention can be used with other classes of B.t. endotoxins to enhance processing of the full-length toxin to obtain the active toxin portion which can have enhanced or expanded activity. The technique would be most applicable to other B.t. toxins which have the characteristic sequence shown in SEQ ID NO. 13.

The subject invention not only includes the novel chimeric toxins and the genes encoding these toxins but also includes uses of these novel toxins and genes. For example, the gene of the subject invention may be used to transform host cells. These host cells expressing the gene and producing the chimeric toxin may be used in insecticidal compositions or, in the case of a transformed plant cell, in conferring insect resistance to the transformed cell itself.

Genes and toxins. The genes and toxins useful according to the subject invention include not only the full length sequences disclosed but also fragments of these sequences, variants, and mutants which retain the characteristic pesticidal activity of the toxin specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The cryIC and cryIA(b) specific genes (or portions thereof which encode toxin or protoxin domains) useful according to the subject invention may be obtained from the recombinant isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 can be used to systematically cut off nucleotides from the ends of these genes. Alternatively, site-directed mutagenesis can be used. Also, genes which encode active fragments may be obtained using a variety of restriction enzymes. Proteases may be used to directly obtain active fragments of these toxins.

Fragments and equivalents which retain the pesticidal activity of the exemplified toxin would be within the scope of the subject invention. Also, as bote above, because of the redundancy of the genetic code, a variety of different DNA sequences can encode the amino acid sequence disclosed herein. It is well within the skill of a person trained in the art to create these alternative DNA sequences encoding the same, or essentially the same, toxin. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying additional toxins and genes useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes,* Stockton Press, New York, N.Y., pp. 169–170. Detection of the probe provides a means for determining in a known manner whether hybridization has occurred. Such a probe analysis provides a rapid method for identifying toxin-encoding genes useful according to the subject invention. Preferably, such genes would be cryIC genes whose core toxin-encoding N-terminal portions can be used with a cryIA(b) protoxin-encoding C-terminal portion to create a chimeric gene according to the subject invention. The nucleotide segments which are used as probes according to the invention can be synthesized using DNA synthesizer and standard procedures. These nucleotide sequences can also be used as PCR primers to amplify genes of the subject invention.

Certain chimeric toxins of the subject invention have been specifically exemplified herein. It should be readily apparent that the subject invention comprises variant or equivalent toxins (and nucleotide sequences encoding equivalent toxins) having the same or similar pesticidal activity of the exemplified toxin. Equivalent toxins will have amino acid homology with the exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same class fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant Hosts. A gene encoding the chimeric toxins of the subject invention can be introduced into a wide variety of microbial or plant hosts. Expression of the toxin gene results, directly or indirectly, in the intracellular production and maintenance of the pesticidal chimeric toxin. With suitable microbial hosts, e.g., Pseudomonas, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the gene encoding the chimeric toxin is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a gene encoding a chimeric toxin into a microorganism host under conditions which allow for the stable maintenance and expression of the gene. These methods are well known to those skilled in the art and are described, for example, in U.S. Pat. No. 5,135,867, which is incorporated herein by reference.

Treatment of cells. As mentioned above, recombinant cells producing the chimeric toxin of the subject invention can be treated to prolong the toxic activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the gene encoding a chimeric toxin of the subject invention, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Hetty's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Since the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the gene encoding a chimeric toxin of the subject invention may be grown in any convenient nutrient medium, where the DNA construct provides a selective advantage, providing for a selective medium so that substantially all or all of the cells retain the recombinant gene. These cells may then be harvested in accordance with conventional methods. Alternatively, the cells can be treated prior to harvesting.

Formulations. Recombinant microbes comprising the gene encoding the chimeric toxin disclosed herein, can be formulated into bait granules and applied to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Materials and Methods

NACS (Bethesda Research Labs, Gaithersburg, Md.) column chromatography was used for purification of electroeluted DNA. Purification was performed according to manufacturer's instructions with the exception that binding buffers were modified to 0.5X TBE/0.2M NaCl and elution buffers were modified to 0.5X TBE/2.0M NaCl.

Random primer labeling of DNA with $^{32}$P was done with a kit (Boehringer-Mannhelm Biochemicals, Indianapolis, Ind.) according to manufacturer's instructions.

Gel purification refers to the sequential application of agarose-TBE gel electrophoresis, electroelution, and NACS column chromatography for the purification of selected DNA fragments, these methods are well known in the art.

Polymerase chain reaction (PCR) amplification of DNA was done for 25 cycles on a Perkin Elmer (Norwalk, Conn.) thermal cycler with the following cycle parameters: 94° C. for 1 minute, 37° C. for 2 minutes, 72° C. for 3 minutes (each 72° C. cycle has a 5 second extension time). PCR products were treated with proteinase K to improve cloning efficiency (Crowe, J. S., Cooper, H. J., Smith, M. A., Sims, M. J., Parker, D., Gewert, D. [1991] *Nucl. Acids Res.* 19:184).

Oligodeoxyribonucleotides (oligonucleotides) were synthesized on an Applied Biosystems (Foster City, Calif.) model 381A DNA synthesizer. Purification was done, when necessary, on Nensorb columns (New England Nuclear-Dupont, Wilmington, Del.), according to the manufacturer's instructions.

Following are examples which illustrate procedures, including the best mode, for practicing the invention. These examples should not be construed as limiting. All percentages are by weight and all solvent mixture proportions are by volume unless otherwise noted.

Example 1—Expression Vector Modification by Splice Overlap Extension

A cloning vector can be constructed based upon pMYC1050, a broad host-range plasmid derived from RSF1010 (pTJS260 can be obtained from Dr. Donald Helinski, U.C. San Diego). An example of the system used in the vector construction may be found in EPO patent application 0 471 564. Plasmid DNA of pMYC1050 initially contained the chimeric toxin gene crylA(c)/crylA(b). The toxin encoded by this gene is described in U.S. Pat. No. 5,055,294. pMYC1050 was constructed by re-cloning the toxin gene and promoter of pM3,130-7 (disclosed in U.S. Pat. No. 5,055,294) into a pTJS260-based-vector such as pMYC467 (disclosed in U.S. Pat. No. 5,169,760) by methods well known in the art. In particular, the pM3,130-7 promoter and toxin gene can be obtained as a BamHI to NdeI fragment and placed into the pMYC467 plasmid, replacing a fragment bounded by the same sites (BamHI near base 12100 and NdeI near base 8000).

The improved vector ideally contains a unique BamHI cloning site. The plasmid BamHI site, located upstream from the tac promoter (ptac), can be removed by blunting with Klenow and re-ligating (FIG. 1). Absence of the site was confirmed by restriction digestion. A plasmid produced according to this procedure was called pMYC1050ΔBamHI. The construct can now have of a BamHI site added to the plasmid by SOE mutagenesis. SOE mutagenesis can be facilitated by subcloning an NsiI toxin-containing DNA fragment from the plasmid into the smaller pGEM5 (Promega Corp., Madison, Wis.) vector which uses the bla gene as a selectable marker (FIG. 1). The fragment can be oriented by restriction digestion. A plasmid produced according to this procedure was called pGEMtox.

Figure 2:
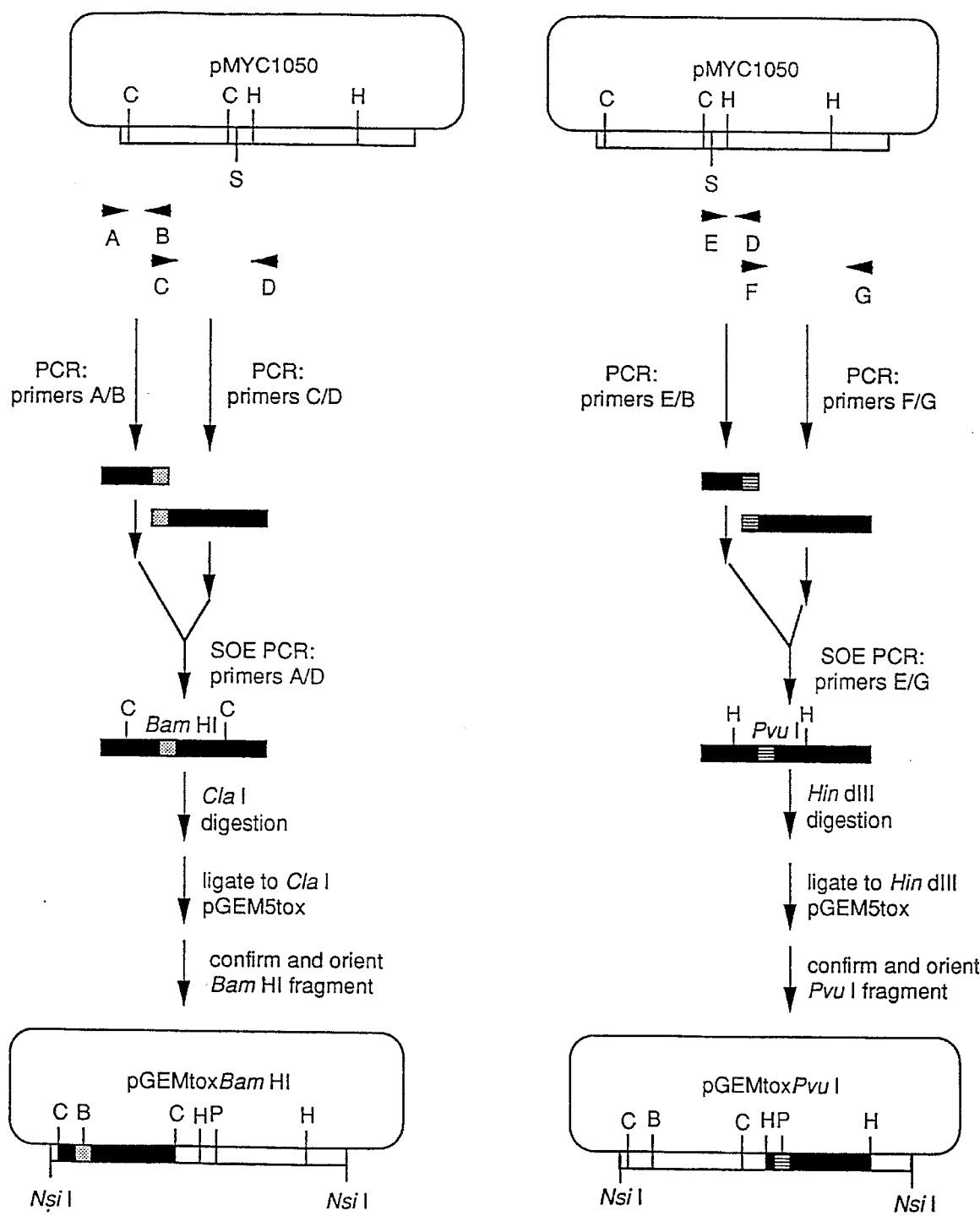
FIG. 2—BamHI or PvuI cloning sites were introduced into toxin DNA by the technique of Splice Overlap Extension (SOE). DNA fragments with the new sites are used to replace homologous DNA fragments in pGEMtox. The resulting plasmids are pGEMtox BamHI or pGEMtox PvuI. The letters A through G below the arrows correspond to oligonucleotide primers in the text. Letters above vertical lines correspond to restriction enzyme sites. B=BamHI, C=ClaI, H=HindIII, P=PvuI, S=SacI.

DNA in the toxin-encoding region was mutated by the PCR-mediated technique of SOE to introduce restriction enzyme cloning sites as shown in FIG. 2. Oligonucleotides used as primers are shown below:

"A" (SEQ ID NO. 1)

5' GCATACTAGTAGGAGATTTCCATGGATAACAATCCGAAC 3'

"B" (SEQ ID NO. 2)

5' GGATCCGCTTCCCAGTCT 3'

"C" (SEQ ID NO. 3)

5' AGAGAGTGGGAAGCGGATCCTACTAATCC 3'

"D" (SEQ ID NO. 4)

5' TGGATACTCGATCGATATGATAATCCGT 3'

"E" (SEQ ID NO. 5)

5' TAATAAGAGCTCCTATGT 3'

"F" (SEQ ID NO. 6)

5' TATCATATCGATCGAGTATCCAATTTAG 3'

"G" (SEQ ID NO. 7)

5' GTCACATAGCCAGCTGGT 3'

Plasmid pMYC1050 DNA was used as the template for PCR amplification using primer sets A/B, C/D, E/D, and F/G. Amplified DNA fragments were named AB, CD, ED, and FG. Amplified DNAs were purified by agarose-TBE gel electrophoresis, electroelution, and NACS column chromatography. Purified template DNAs were used in a second set of PCR reactions. Fragments AB and CD were mixed and amplified with primers A and D. In a separate reaction, fragments ED and FG were mixed and amplified with primers E and G. Amplified DNA was resolved by agarose-TBE gel electrophoresis and the fragments with the corresponding increase in size were excised, electroeluted, and purified. Amplified DNA fragments are called AD or EG for reference.

DNA fragments AD or EG with the new restriction enzyme sites were incorporated into the toxin-containing DNA by several subcloning experiments (FIGS. 2 and 3). pGEMtox was digested with ClaI or HindIII. Vector toxin-containing DNA was gel-purified. Fragment AD was digested with ClaI and ligated to ClaI-digested pGEMtox vector DNA. Fragment EG was digested with HindIII and ligated to HindIII-digested pGEMtox vector DNA. *E. coli* strain NM522 was transformed with ligation mixes. Correctly assembled constructs were identified by restriction enzyme digestion of plasmid DNA from isolated colonies. The plasmid with the new BamHI site was called pGEMtox BamHI. The plasmid with the new PvuI site was called pGEMtox PvuI. The ClaI fragment containing the BamHI site from plasmid pGEMtox BamHI was ligated to the phosphatased ClaI vector-containing fragment from pGEMtox PvuI. *E. coli* strain NM522 was transformed with ligation mixes. Correctly assembled constructs were identified by PCR analysis with primer set C/D, and by restriction digestion. The plasmid with both new restriction enzyme sites was called pGEMtox BamHI/PvuI.

Figure 3:
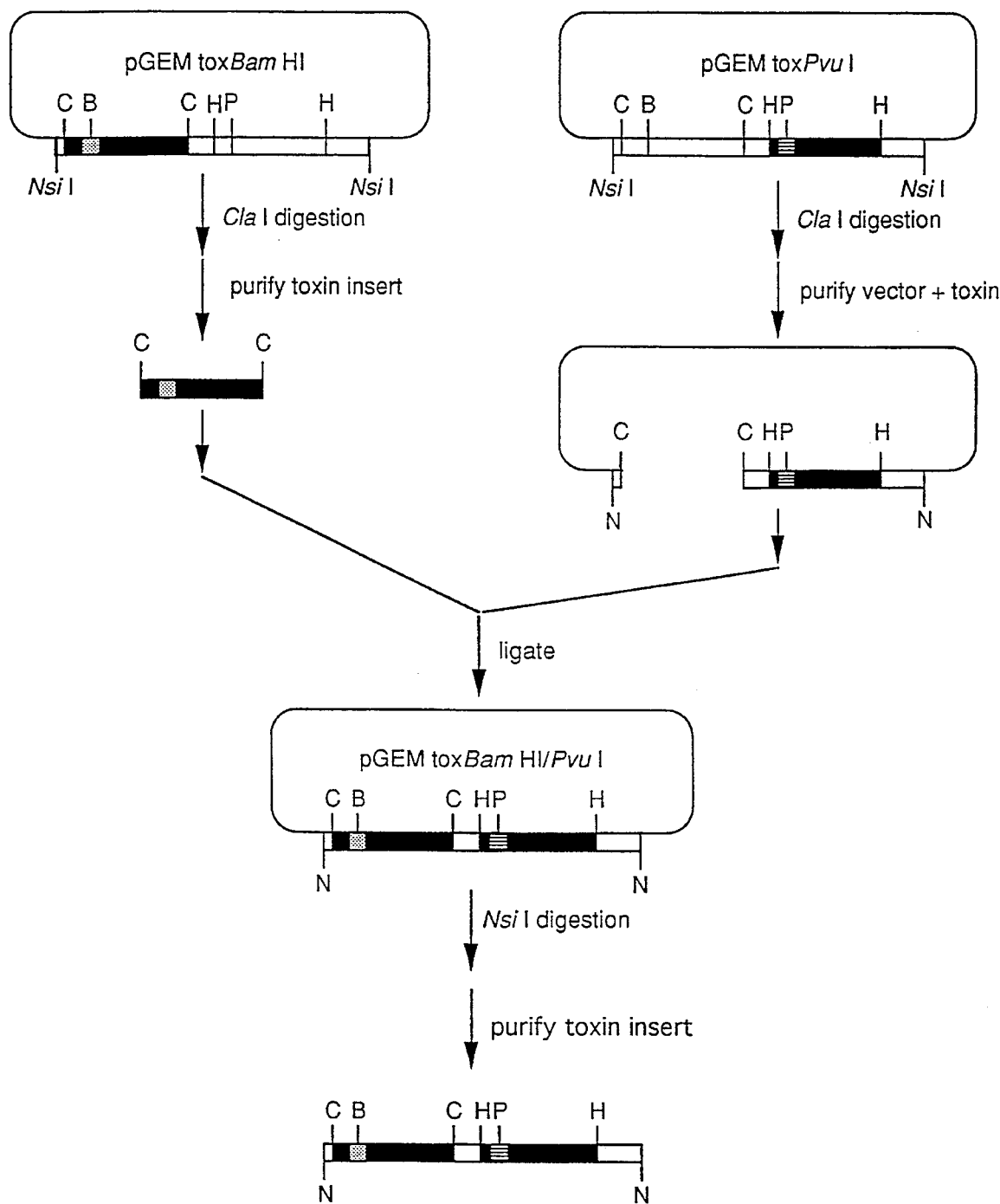
FIG. 3—The DNA fragment containing the BamHI mutation is used to replace the homologous fragment in pGEMtox PvuI. The resulting plasmid which contains both cloning sites is pGEMtox BamHI/PvuI. To construct an expression plasmid, the toxin-containing NsiI fragment is excised for cloning into the pTJS260 broad host-range vector. B=BamHI, C=ClaI, H=HindIII, P=PvuI.
Figure 4:
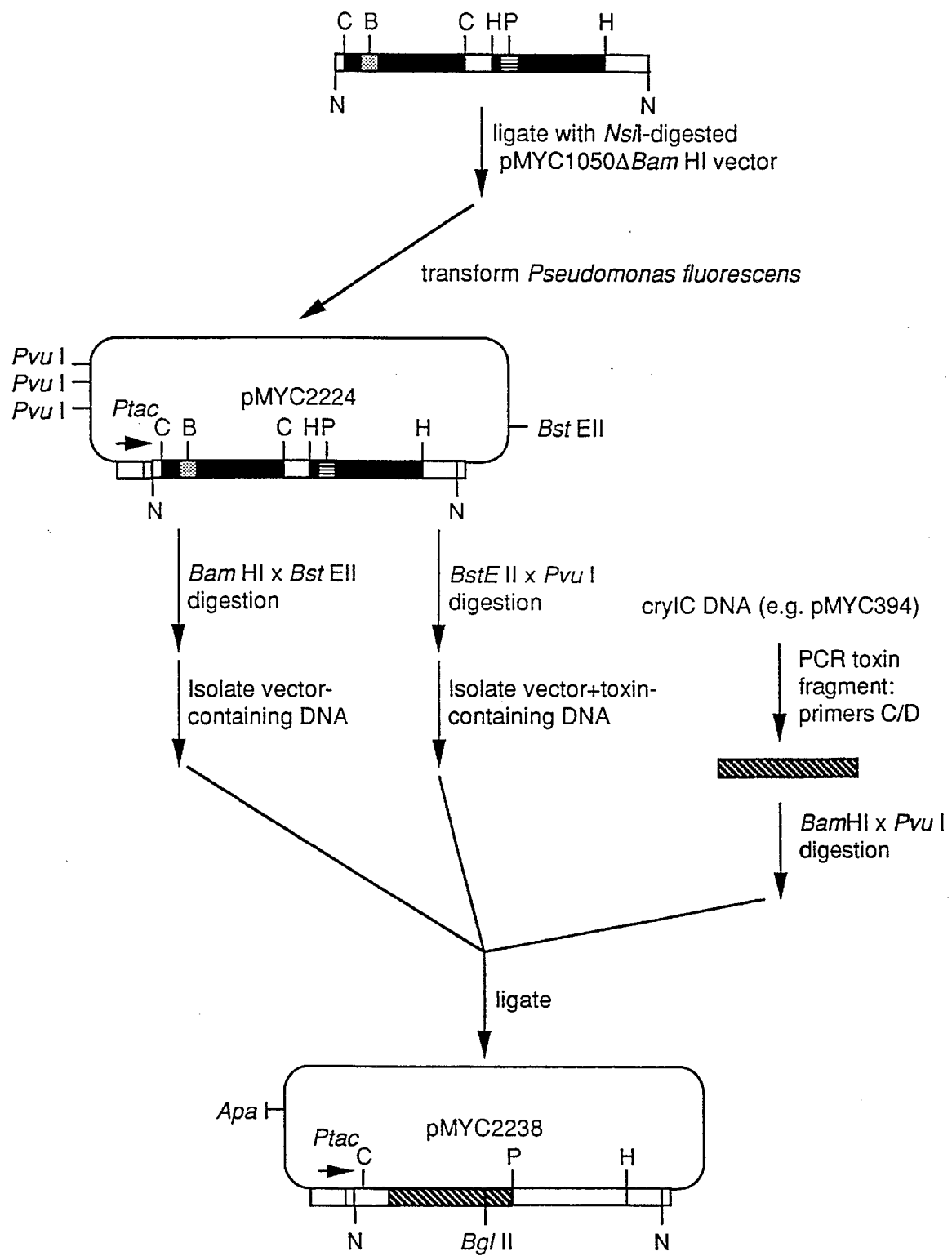
FIG. 4—The NsiI toxin-containing fragment with the new restriction sites is ligated to the vector-containing DNA from pMYC1050ΔBamHI to give pMYC2244. A BamHI-PvuI PCR-derived DNA fragment containing the cryIC toxin is exchanged for the equivalent fragment in pMYC2244. The resulting chimera is called pMYC2238. B=BamHI, C=ClaI, H=HindIII, N=NsiI, P=PvuI.

A completed expression vector was assembled with the insert from pGEMtox BamHI/PvuI and the vector from pMYC1050ABamHI (FIGS. 3 and 4). Gel-purified insert was prepared from pGEMtox BamHI/PvuI by NsiI digestion, and ScaI digestion (to remove contaminating vector). It was ligated to gel-purified NsiI-digested vector-containing pMYC1050ΔBamHI DNA. *E. coli* strain NM522 was transformed with the ligation mixes, and transformation mixes were plated on LB agar containing tetracycline at 12 µg/ml. Colonies containing the NsiI insert were identified by colony hybridization and autoradiography. Inserts were oriented by PCR, using primer set A/D, which bridges a NsiI cloning site, and agarose-TBE gel electrophoresis. The correctly assembled plasmid is called pMYC2224. A lactose-inducible *P. fluorescens* strain was electroporated with correctly assembled plasmid DNA. Transformation mixes were plated on LB agar containing tetracycline at 20 µg/ml. Plasmid DNA was prepared from *P. fluorescens* for use in subsequent cloning experiments.

Example 2—Subcloning the crylC Hypervariable Region into pMYC2224

A DNA fragment containing the hypervariable region of the crylC gene is obtained by PCR using primers C and D (SEQ ID NOS. 3 and 4, respectively, from *Bacillus thuringiensis* DNA (e.g., PS81I) or a plasmid with cloned DNA (e.g., pMYC394) containing crylC. The resulting PCR fragment was digested with restriction enzymes BamHI and PvuI and purified following agarose gel electrophoresis. Since the tetAR gene contains multiple PvuI sites, it was necessary to isolate the vector-containing DNA on two separate fragments. To obtain the first fragment, pMYC2224 was digested with BamHI×BstEII, and the large DNA fragment containing the promoter-tetAR locus-rep functions was gel-purified. To obtain the second fragment, pMYC2224 was digested with BstEII×PvuI, and the DNA fragment containing the vector-protoxin module was gel-purified. A three-piece ligation was set up and used for *E. coli* strain NM522 transformation. Plasmids were recovered following transformation of *E. coli* containing the correct inserts, as judged by restriction enzyme digestion.

The correct plasmid is named pMYC 2238. The plasmid consists of crylA(c) at the amino-terminus, crylC up to the toxin/protoxin junction, and crylA(b) through the protoxin segment.

Example 3—Construction of a Native crylC and a Chimeric crylC/crylA(b) Protoxin Expression Plasmids An expression plasmid containing the crylC gene can be constructed using a three-fragment ligation as follows: (1) digestion of pMYC394 (from NRRL B-18500) with HindIII with subsequent purification of a 26 4600 bp fragment containing the crylC gene; (2) digestion of pTJS260, from which the SacI (bp 214) to NotI (bp 1674) had been deleted (described in EP 0 471 564 A2) with EcoRI and HindIII with subsequent purification of the ≈6300 bp fragment containing the plasmid replication origin; (3) digestion of pMYC1197 (described in EP 0 471 564 A2) with EcoRI and SpeI followed by purification of an ≈4200 bp fragment containing the tetracycline resistance genes and ptac promoter. The three fragments are ligated together and transformed into a lactose-inducible *P. fluorescens* using electroporation. The resulting tetracycline-resistant colonies are screened for plasmids having the correct structure.

Figure 5:
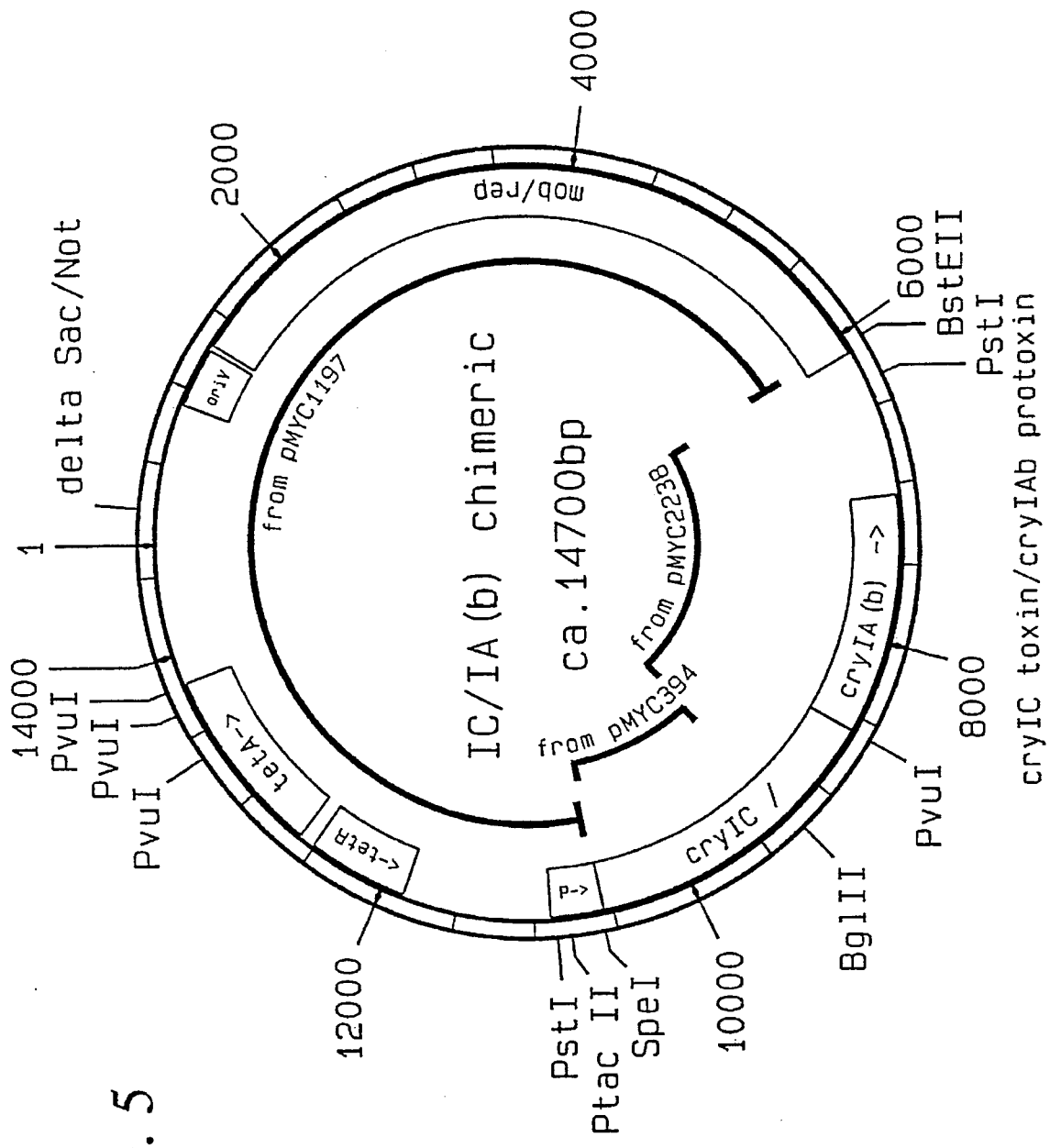
FIG. 5—A restriction map of a plasmid carrying a chimeric gene of the subject invention.

An expression plasmid containing the crylC/crylA(b) chimeric gene can be constructed by digesting pMYC2238 with BglII and BstEII and purifying the ≈3200 bp fragment. A second fragment can be produced by digesting the crylC expression plasmid above with the same enzymes and subsequent purification of an ≈12000 bp fragment. The fragments are ligated together and transformed into a lactose-inducible *P. fluorescens* using electroporation. The resulting tetracycline-resistant colonies are screened for plasmids having the structure indicated in FIG. 5 by restriction enzyme digestion and agarose gel analysis.

U.S. Pat. No. 5,169,760 discloses means for making *P. fluorescens* capable of regulating β-galactoside-inducible promoters. This patent and EP 0 471 564 A2 describe conditions for expression of these genes in *P. fluorescens*.

Example 4—Activity of the Chimeric Toxin Against *Spodoptera exigua*

Serial dilutions of recombinant *Pseudomonas fluorescens* stabilized by the methods disclosed in U.S. Pat. Nos. 4,695, 455 and 4,695,462 were mixed with modified USDA soy flour insect diet (Technical Bulletin 1528, U.S. Department of Agriculture). This mixture was poured into plastic trays with compartmentalized 3-ml wells (Nutrend Container Corporation, Jacksonville, Fla.). Water served as a control as well as the vehicle to introduce the toxin protein into the diet. Second-instar *Spodoptera exigua* larvae were placed singly onto the diet mixture. Wells were then sealed with MYLAR sheeting (ClearLam Packaging, Ill.) using a tacking iron, and several pinholes were made in each well to provide gas exchange. Larvae were held with continuous light at 25° C. or 29° C. and mortality was recorded after six or four days, respectively. $LC_{50}$s were determined by standard log-probit analysis (POLO-PC, LeOra Software, 1987). CrylC and the crylC/crylA(b) chimeric were tested simultaneously and representative results are as follows:

TABLE 2

| Toxin Designation | LC50 (µg toxin/ml diet) |
| --- | --- |
| crylC | 139 |
| crylC/crylA(b) | 28 |

Example 5—Insertion of the Gene Encoding the Chimeric Toxin Into Plants

One aspect of the subject invention is the transformation of plants with genes encoding the insecticidal toxin. The transformed plants are resistant to attack by the target pest.

The gene encoding the chimeric toxin, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 0 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobactedum tumefaciens* or *Agrobactedum rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed traits to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic genes for use in plants are known in the art.

Example 6—Cloning of the Gene Encoding the Chimeric Toxin Into Insect Viruses A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise the chimeric toxin gene are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated DNA molecule comprising a nucleotide sequence encoding a chimeric *Bacillus thuringiensis* toxin of approximately 1150 to 1200 amino acids, wherein said toxin comprises a cryIC core N-terminal toxin portion having a sequence of at least about 600 amino acids and no more than about 1100 amino acids, wherein the amino acid sequence from the end of said core N-terminal sequence to the C-terminus of the chimeric toxin is a cryIA(b) C-terminal protoxin portion having a cryIA(b) sequence.

2. The isolated DNA molecule, according to claim 1, wherein said core toxin portion comprises the first about 616 amino acids of a cryIC toxin and wherein said protoxin portion comprises the amino acids from about 1058 of SEQ ID NO. 11 to the C-terminus of the cryIA(b) toxin.

3. The isolated DNA molecule, according to claim 1, which is a toxin having an amino acid sequence as shown in SEQ ID NO. 12.

4. The isolated DNA molecule, according to claim 1, wherein the transition from cryIC sequence to cryIA(b) occurs after the sequence shown in SEQ ID NO. 13 and before a sequence corresponding to positions 1050 to 1057 of SEQ ID NO. 11.

5. A recombinant DNA transfer vector comprising a DNA molecule of claim 1.

6. The isolated DNA molecule, according to claim 2, which encodes a toxin having the amino acid sequence shown in SEQ ID NO. 11.

7. A recombinant host transformed to express a chimeric *Bacillus thuringiensis* toxin comprising a cryIC core N-terminal toxin portion and a cryIA(b) C-terminal protoxin portion.

* * * * *

UNITED STATES PATENT AND TRADEMARK OFFICE
CERTIFICATE OF CORRECTION

PATENT NO. : 5,593,881

DATED : January 14, 1997

INVENTOR(S) : Thompson *et al.*

It is certified that error appears in the above-identified patent and that said Letters Patent is hereby corrected as shown below:

Column 1, line 46: "*tenebdonis*" should read --*tenebrionis*--

Column 2, line 20: "haft" should read --half-- line 22: "cry1IIA" should read --cryIIIA-- line 43: "cry1C and Cry1A(b)" should read --cryIC and cryIA(b)-- line 47: "cry1C" should read --cryIC-- line 51: "cry1C and cry1A(b)." should read --cryIC and cryIA(b).-- line 66: "cry1A(b)" should read --cryIA(b)-- line 67: "crylC protoxin segment. The cryIC/crylA(b)" should read --cryIC protoxin segment. The CryIC/ryIA(b)

Column 3, line 1: "crylC/crylC" should read --cryIC/cryIC-- line 6: "crylC" should read --cryIC-- line 7: "crylA(b)" should read --cryIA(b)-- line 37: "polymeruse" should read --polymerase-- line 41: "HindlII" should read --HindIII-- line 50: "HindlII" should read --HindIII--

UNITED STATES PATENT AND TRADEMARK OFFICE
CERTIFICATE OF CORRECTION

PATENT NO. : 5,593,881

DATED : January 14, 1997

INVENTOR(S) : Thompson *et al.*

It is certified that error appears in the above-identified patent and that said Letters Patent is hereby corrected as shown below:

Column 3, line 57: "HindlII" should read --HindIII-- line 65: "HindlII" should read --HindIII--

Column 4, line 28: "crylA(b)" should read --cryIA(b)-- line 29: "cry1C" should read --cryIC-- line 55: "crylA(c)/crylA(b)" should read --cryIA(c)/cryIA(b)-- line 59: "crylC" should read --cryIC-- line 60: "crylC-containing" should read --cryIc-containing--.

lines 61&62: "crylA(c)/crylA(b)" should read --cryIA(c)/cryIA(b)-- line 64: "crylA(c) followed by crylC" should read --cryIA(c) followed by cryIC-- line 65: "crylA(b)" should read --cryIA(b)-- line 67: "crylC" should read --cryIC--

Column 5, line 3: "crylC" should read --cryIC-- line 4: "crylA(b)" should read --cryIA(b)--

UNITED STATES PATENT AND TRADEMARK OFFICE
CERTIFICATE OF CORRECTION

PATENT NO. : 5,593,881

DATED : January 14, 1997

INVENTOR(S) : Thompson *et al.*

It is certified that error appears in the above-identified patent and that said Letters Patent is hereby corrected as shown below:

Column 5, line 5: "cryIC" should read --cryIC-- line 16: "cryIC" should read --cryIC-- line 17: "cryIC" should read --cryIC-- line 46: "cryIC" should read --cryIC-- line 49: "cryIA(b)" should read --cryIA(b)--

Column 6, line 4: "cryIC" should read --cryIC-- line 25: "Blochem." should read --Biochem.--

Column 7, line 3: "cryIC and cryIA(b)" should read --cryIC and cryIA(b)-- line 14: "Ba131" should read --Bal31-- line 52: "cryIC" should read --cryIC-- line 54: "cryIA(b)" should read --cryIA(b)--

Column 8, line 67 & Column 9, line 1: "Agrobacterium," should read

--Agrobacterium,--

Column 9, line 12: "diffiuens" should read --diffluens--

UNITED STATES PATENT AND TRADEMARK OFFICE
CERTIFICATE OF CORRECTION

PATENT NO.    :    5,593,881

DATED         :    January 14, 1997

INVENTOR(S)   :    Thompson et al.

It is certified that error appears in the above-identified patent and that said Letters Patent is hereby corrected as shown below:

Column 11, line 6: "Mannhelm" should read --Mannheim-- line 43: "crylA(c)/crylA(b)" should read --cryIA(c)/cryIA(b)--

Column 12, line 42: "HindlII" should read --HindIII-- line 45: "HindlII" should read --HindIII-- line 46: HindlII" should read --HindIII--

Column 13, line 13: "crylC" should read --cryIC-- line 16: "crylC" should read --cryIC-- line 19: "crylC" should read --cryIC-- line 34: "crylA(c)" should read --cryIA(c)-- line 34: "crylC" should read --cryIC-- line 35: "crylA(b)" should read --cryIA(b)-- line 38: "crylC" should read --cryIC-- line 39: "crylA(b)" should read --cryIA(b)-- line 42: "crylC" should read --cryIC-- line 44: "HindlII" should read --HindIII--

UNITED STATES PATENT AND TRADEMARK OFFICE
CERTIFICATE OF CORRECTION

PATENT NO. : 5,593,881

DATED : January 14, 1997

INVENTOR(S) : Thompson *et al.*

It is certified that error appears in the above-identified patent and that said Letters Patent is hereby corrected as shown below:

Column 13, line 45: "a 26 4600" should read --a ≈ 4600-- line 46: "cryIC" should read --cryIC-- line 48: "HindlII" should read --HindIII-- line 58: "cryIC/cryIA(b)" should read --cryIC/cryIA(b)-- line 59: "BglII" should read --BglII-- line 61: "cryIC" should read --cryIC--

Column 14, line 24: "CryIC and the cryIC/cryIA(b)" should read

--CryIC and the cryIC/cryIA(b)--

Column 15, line 14: "*Agrobacteriurn tumefaciens*" should read --*Agrobacterium tumefaciens*-- line 37: "*Agrobactedum tumefaciens*" should read --*Agrobacterium tumefaciens*-- ine 38: "*Agrobactedum rhizogenes*" should read --*Agrobacterium rhizogenes*--

Column 31, line 52: "cryIC" should read --cryIC-- line 56: "cryIA(b)" should read --cryIA(b)-- line 57: "cryIA(b)" should read --cryIA(b)

UNITED STATES PATENT AND TRADEMARK OFFICE
CERTIFICATE OF CORRECTION

PATENT NO. : 5,593,881

DATED : January 14, 1997

INVENTOR(S) : Thompson *et al.*

It is certified that error appears in the above-identified patent and that said Letters Patent is hereby corrected as shown below:

Column 31, line 60: "crylC" should read --cryIC-- line 62: "crylA(b)" should read --cryIA(b)--

Column 32, line 60: "crylC" should read --cryIC-- line 61: "crylA(b)" should read --cryIA(b)--

Signed and Sealed this

Eighteenth Day of November 1997

Attest:

BRUCE LEHMAN

Attesting Officer

Commissioner of Patents and Trademarks